(12) United States Patent
Pasqui et al.

(10) Patent No.: US 11,982,576 B2
(45) Date of Patent: May 14, 2024

(54) MONITORING SYSTEM FOR PERISHABLE PRODUCTS

(71) Applicants: Valentina Pasqui, Umbertide PG (IT); Ori Faran, Zichron Yaakov (IL)

(72) Inventors: Valentina Pasqui, Umbertide PG (IT); Ori Faran, Zichron Yaakov (IL)

( * ) Notice: Subject to any disclaimer, the term of this patent is extended or adjusted under 35 U.S.C. 154(b) by 200 days.

(21) Appl. No.: 17/625,418

(22) PCT Filed: Jul. 8, 2020

(86) PCT No.: PCT/IB2020/056419
§ 371 (c)(1),
(2) Date: Jan. 7, 2022

(87) PCT Pub. No.: WO2021/005525
PCT Pub. Date: Jan. 14, 2021

(65) Prior Publication Data
US 2022/0252461 A1    Aug. 11, 2022

Related U.S. Application Data

(60) Provisional application No. 62/871,321, filed on Jul. 8, 2019.

(51) Int. Cl.
*G01K 3/04* (2006.01)
*G01K 11/12* (2021.01)
*G06K 19/06* (2006.01)
*G01N 33/02* (2006.01)

(52) U.S. Cl.
CPC .......... *G01K 3/04* (2013.01); *G01K 11/12* (2013.01); *G06K 19/06037* (2013.01); *G01N 33/02* (2013.01)

(58) Field of Classification Search
CPC ...... G01K 11/12; G01K 3/04; G06K 19/0615; B41M 3/14; C09D 11/50; G01N 31/22
See application file for complete search history.

(56) References Cited

U.S. PATENT DOCUMENTS

| | | | | |
|---|---|---|---|---|
| 5,686,153 A | * | 11/1997 | Heynderickx | C09K 19/3833 428/1.32 |
| 10,074,047 B2 | | 9/2018 | Hyde | |
| 2008/0269050 A1 | * | 10/2008 | Azizian | G01N 31/229 374/E3.004 |
| 2018/0100807 A1 | * | 4/2018 | Abdo | G01N 21/78 |
| 2018/0129921 A1 | * | 5/2018 | Hyde | B41M 3/14 |
| 2021/0034831 A1 | * | 2/2021 | Abdo | G01K 3/04 |

OTHER PUBLICATIONS

International Search Report and Written Opinion in International Patent Application No. PCT/IB2020/056419, dated Aug. 17, 2020 (13 pages).

* cited by examiner

*Primary Examiner* — Mirza F Alam
(74) *Attorney, Agent, or Firm* — Nixon Peabody LLP

(57) ABSTRACT

The present invention provides a combine system in the present invention can be used as dual propose temperature monitoring indicator.

The system comprises of scanning devise, QR barcode and temperature indicator providing visual characteristic, which changed depending on time and temperature after triggering, had occurred. The device is not susceptible to environmental conditions and can be stored in room temperature.

5 Claims, 2 Drawing Sheets

MONITORING SYSTEM FOR PERISHABLE PRODUCTS

CROSS-REFERENCE TO RELATED APPLICATIONS

This patent application is a U.S. national stage of International Application No. PCT/IB2020/056419, filed Jul. 8, 2020, which claims priority and benefit of U.S. patent application No. 62/871,321 filed on Aug. 7, 2019, each of which is hereby incorporated by reference.

FIELD OF THE INVENTION

The present invention relates to a system that enables real time monitoring of perishable products during supply chain and afterwards. More particularly, the present invention relates to a system which combines scanning device, QR barcode and temperature sensitive indicator that irreversibly change color with time in such a manner that the change is faster at elevated temperatures and slower at lower temperatures.

BACKGROUND OF THE INVENTION

Many products are transported and sold to an end user in refrigerated conditions since they are sensitive to temperature. They can be damaged not only by exposure the higher or lower temperatures than the recommended ones, but also due to the exposure time from the production date even if they are kept in recommended temperature. The most common examples include food, drugs, organic chemicals and biologic materials.

Therefore, there is a need to print expiration date on those products. The problem is that expiration date assumes a certain temperature exposure during the shelf life of the product but cannot indicate the actual time and temperature exposure of the product before reaching the end user. This results in either the sale of a spoiled product or premature disposal of good product.

The only solution to this problem is to attach to the perishable product an irreversible temperature indicator, which enables real time true information on product condition.

Temperature Indicators are divided into two categories;

The first one temperature indicator (TI) generates a signal alarm by a color change only if the product was exposed to certain critical threshold temperature (above or below).

The second one time-temperature-indicator (TTI) integrates time over any temperature and therefore its output is a continuous color change from the time of activation, until it reaches final color. This signal the product was exposed to the integral sum of predetermine duration over the recommend temperature.

Both categories have disadvantages.

Although the TI warns of extreme temperature exposure abuse during the storage/shipping stages. It lacks the ability to signal the user of passed shelf life, since it's not time sensitive.

Another main disadvantage of the current TI is the lack of ability to control the duration time of the temperature abuse, which is very short in the known TIs. This can lead to false classification of non-safe to use product, even after short temperature abuse, which did not significant damage it.

Another disadvantage of the current TI is the lack of ability to control the magnitude of the temperature abuse, which is very small in the known TIs. This can lead to false classification of non-safe to use product, even after small temperature abuse, which did not significant damage it.

On the other hand, the TTI can warn on passed shelf life, but cannot warn on any temperature abuse, this can only speed the indication of the end color.

Some attempts have been made and various patents have been issued describing a temperature indicator combined with bar code designed to be attached to a package and indicate when a package has been temperature abused or has reached the end of its safe shelf life.

They all use one of the two operation modes:
1. The bar code is made from color changing material, so the barcode reading changes as response to temperature change. For example, Nemet et al (U.S. Pat. Nos. 10,303,992, 10,262,251, 10,089,566, 10,037,507, 9,996,783, 9,836,678, 9,710,743, 9,646,277, 9,646, 237, 9,626,610, 9,558,439, 9,396,423, 9,373,100). Hyde et al (U.S. Pat. Nos. 10,074,047, 9,779,346, 9,779,346). Lee et al. (U.S. Pat. Nos. 9,476,083, 9,134, 287).
2. The barcode is printed on color change layer, which when changing color makes the bar code non-readable. For example, Ribe et al. (U.S. Pat. Nos. 9,709,539, 8,569,208). Azizian et al. U.S. Pat. No. 8,629,081. Norrby et al. WO2004050507. Patel et al. (U.S. Pat. Nos. 8,343,437, 5,045,283).

The disadvantages of the first operation mode indicators are described hereinafter.

Firstly, the ones that use melting materials as active indicators must be stored at low temperatures prior to their attachment to the product (or need manual activation). Also, they will not work if the indicator attached upside down or if the product is shipped upside down due to luck of gravity.

These requirements greatly increase the cost of those indicators, complicate the production line procedures and introduce an element of uncertainty as to the reliability of the indicators.

Secondly, if the barcode is damaged during shipment, or the scanner cannot scan it for any reason, the user is left with no option to know the condition of the product.

Thirdly, the temperature range of such indicators is limited.

The main disadvantage of second operation mode indicators described herein, is that different scanners have different sensitivity to different colors and backgrounds. Therefore, non-readable barcode could be the result of less/more scanner sensitivity leading to misleading output.

Therefore, there is a need for a new system that can overcome all those disadvantages by combine the two operation modes, with wide range of abuse temperature and duration, and that the temperature indicator can be activated at the site of application.

SUMMARY OF THE INVENTION

It is an object of the present invention to provide a combined system that can be used as dual propose temperature indicator (TTI and TI).

It is another object of the present invention to provide a chemical colorimetric indicating device adapted to allow visual detection of time and temperature exposures.

It is another object of the present invention to provide a QR barcode integrated with temperature indicator, is such way which will enable the user to receive by scanning indication on the true condition of the perishable product.

It is another object of the present invention to provide a window in the QR barcode to enable visual scanning of the changing color by the scanning device and the human eye.

It is another object of the present invention to provide a system in which that the indicator will have wide range of critical temperature and can indicate temperature abuse both above and below abuse of critical temperature.

It is another object of the present invention to provide a scanning device with a specific application that has a data base of the color change values of the specific indicator and threshold temperatures and duration allowed.

It is another object of the present invention to provide printed serial number below the QR barcode that will prevent counterfeiting.

It is another object of the present invention to provide that chemical colorimetric reaction of indicator intended to be engaged with a product is sensitive to temperature and time so that an exact indication of the product condition is exhibited at any time.

It is yet another object of the present invention to provide a chemical colorimetric indicator that is provided with a triggering mechanism allowing the chemical reaction to start at a predetermined instant, and be manufacture, ship and store in room temperature before activated.

An additional object of the present invention is to provide a chemical colorimetric indicator that is not susceptible to environmental conditions that can affect the accuracy of the indicator or uses toxic substances.

It is thus provided in accordance with a preferred embodiment of the present invention an indicator capable of exhibiting a time-temperature dependence and temperature depended comprising:

at least one first reactant selected from a group of materials such as: redox reactions, chelating agents, PH sensitive dye and metal etching acid and free radical generators that usually form radical that destroys the dye molecule;

at least one second reactant from that group adapted to react according to a predetermined chemical reaction with said at least one first reactant upon triggering wherein a visual characteristic is changed depending on time and temperature after triggering had occurred.

Furthermore, in accordance with another preferred embodiment of the present invention, said top label and base label are initially provided separately while a manufacturer attaches said first label and said second label together in order to start activation of the reaction.

Furthermore, in accordance with another preferred embodiment of the present invention, said top label and said base label are separated by impervious removable film that can be removed by an end user at any desirable time.

Furthermore, in accordance with another preferred embodiment of the present invention, said barrier layer printed on the top of the base label is a clear polymeric matrix that is adapted to allow diffusion of said at least one first reactant through said barrier as a function of temperature wherein said at least one second reactant is prevented from diffusing through said barrier layer.

Furthermore, in accordance with another preferred embodiment of the present invention, said barrier layer is in the substantial range of 5-200 microns in thickness. Furthermore, in accordance with another preferred embodiment of the present invention, said at least one first reactant is a nonvolatile solution of concentration of substantially 0.01-5%.

Furthermore, in accordance with another preferred embodiment of the present invention, said at least one second reactant is a nonvolatile solution having concentration of substantially 0.1-5%.

Furthermore, in accordance with another preferred embodiment of the present invention, the base label further comprises adhesive layer adapted to allow adhering of the indicator to a product.

BRIEF DESCRIPTION OF THE FIGURES

In order to better understand the present invention and appreciate its practical applications, the following Figures are attached and referenced herein. Like components are denoted by like reference numerals.

It should be noted that the figures are given as examples and preferred embodiments only and in no way limit the scope of the present invention as defined in the appending Description and Claims.

DETAILED DESCRIPTION OF THE INVENTION

The present invention provides a System comprising a Scanning device with special software, QR barcode and time-temperature indicator. The System can be used as dual propose temperature indicator (TTI and TI). The indicator is capable of exhibit a time-temperature dependence by visually detectable chemical reaction between reactants as a result of trigger activation of composition. The indicator comprises at least two reactants adapted to react upon triggering wherein a visual color is changed depending on time and temperature after triggering had occurred and a matrix adapted to carry said at least two reactants wherein the chemical reaction is performed on said matrix. The triggering modernism is by attaching one label onto print base layer preprinted on the package perishable product or mixing two cartridges and printing on the package of perishable product. The indicator can to be manufacture, ship and stored in room temperature before activation. The temperature exposure history of the product creates a color change signal which is detectable to the observer eye.

Preferred active compounds are those that participate in an immediate color change process. There are known double reactants processes such as metal ions and chelating agents, redox processes that change color due to a change in the oxidation state of individual specie, pH dependent color change indicators, metal foil etching acid that expose color below the foil, and free radical generators that usually form radical that destroys the dye molecule.

One of the most important advantage of these reactants is that they react solely with their pairs; therefore, are not sensitive to environmental conditions.

In order to obtain the widest possible range of indicator response in one recording material, the recording material can contain a mixture of different indicator compounds, each of which undergoes a series of color changes during thermal history development.

These are fast processes that form/deform color in direct contact and therefore must be manipulated by a second, temperature-controlled process, such as migration throw barrier.

Reference is now made to FIG. 1 illustrating a device capable of exhibiting a time-temperature dependence in accordance with a preferred embodiment of the present invention.

Figure 1A:
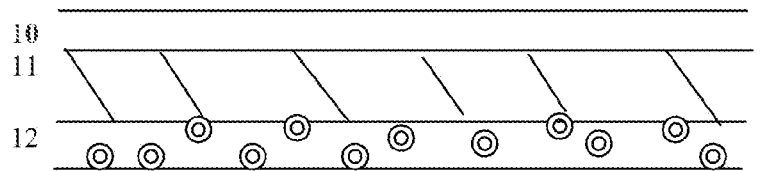
FIG. 1a illustrates a two-label system indicating apparatus capable of exhibiting time-temperature dependence in accordance with a preferred embodiment of the present invention. Layer 10 is the QR barcode layer. Layer 11 is a transparent film. Layer 12 is made of glue mix with first reactant coated at the bottom of layer 11. Layer 13 is a clear polymer/ink barrier printed on layer 14. Layer 14 is made of ink mix with second reactant printed on layer 15. Layer 15 is a polymer base film with self-adhesive glue.
Figure 1A:
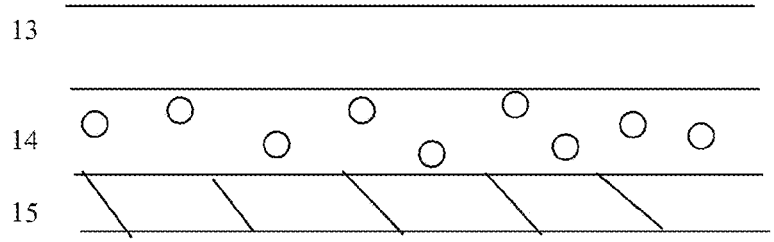
Figure 1B:
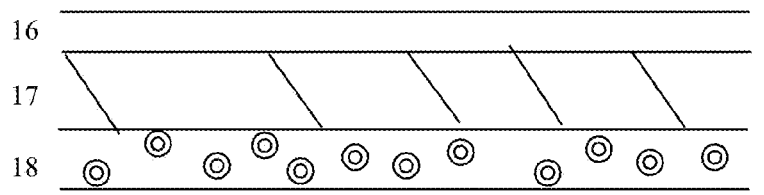
FIG. 1b illustrates a single label system (the second one printed on the package by the package manufacture), indicating apparatus capable of exhibiting time-temperature dependence in accordance with a preferred embodiment of the present invention. Layer 16 is the QR barcode layer printed on white background on layer 17. Layer 17 is a transparent film. Layer 18 is made from glue mix with first reactant coated at the bottom of layer 17. Layer 19 is a clear ink barrier printed on layer 20. Layer 20 is made from ink mixes with second reactant printed on the package.
Figure 1B:
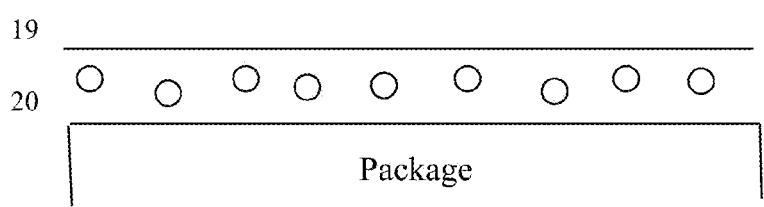
Figure 1C:
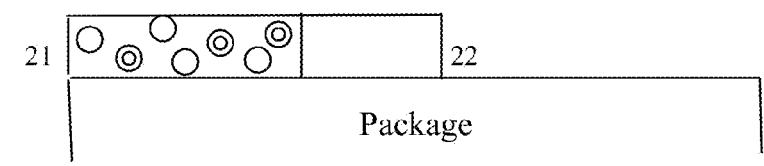
FIG. 1c Illustrates an indicating apparatus capable of exhibiting time-temperature dependence in accordance with a preferred embodiment of the present invention. The system comprises layers of reactants solutions mix with transparent ink. Layer 21 is made of inks layers with mix of reactants with/without ink barrier printed on the package. Layer 22 is QR barcode printed on the package beside or around layer 21.
Figure 2:
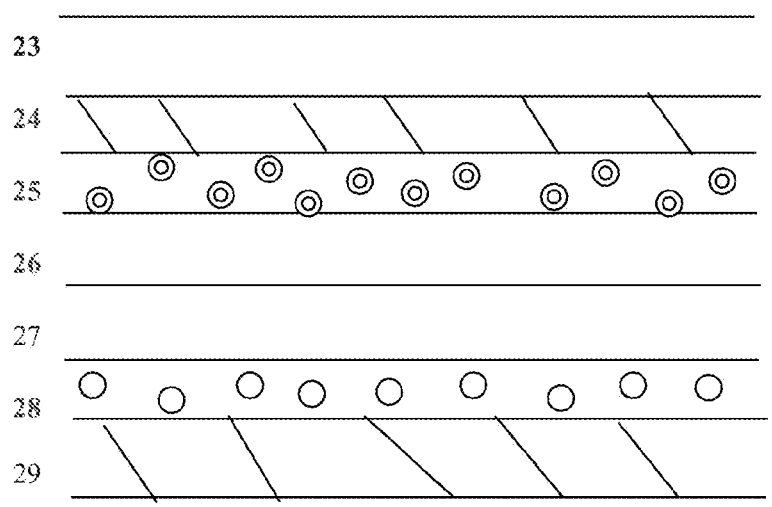
FIG. 2 Illustrates one label system indicating apparatus capable of exhibiting time-temperature dependence in accordance with a preferred embodiment of the present invention. Layer 23 is the QR barcode layer. Layer 24 is a transparent film. Layer 25 glue mixes with first reactant coated at the bottom of layer 24. Layer 26 is a separate film that end user can remove and activate the indictor. Layer 27 is a clear polymer/ink barrier printed on layer 28. Layer 28 ink mixes with second reactant printed layer 29. Layer 29 is polymer film with self-adhesive.
Figure 3:
FIG. 3 illustrates an QR barcode printed around (or beside) the temperature indicator, leaving clear area of the indicator, to allow visible indication at any case and scanning of the indicator, in accordance with a preferred embodiment of the present invention.

There are 3 options of implementing the temperature indicator to the perishable package:

1. In the first option, the indicator comprises two labels (FIG. 1a). The first label is the top label composed of a QR barcode printed in black around a rectangle clear area of the indicator (FIG. 3), to allow visual sign of the color change, on the top label, which is made from transparent film coated on the bottom with glue mixes containing the first reactant. The second label is the base label printed with two layers, a clear barrier layer a below a layer of ink mixes with the second reactant. The base label is made from polymer film with self-adhesive glue layer on the bottom in order to attach it to the product package. The product manufacture will receive the two labels, attach them to the product package after packaging one on top of the other and by so activate the indicator.
2. In the second option (FIG. 1b), only the top label is provided to the product manufacture. The ink with the second reactant layer and barrier layer is provided to the package manufacture, which prints it on the package. The product manufacture only attaches the first label on the printed base layer, which is on the package of the perishable product after packaging and by so activate the temperature indicator.
3. In the third option (FIG. 1c), the product manufacture is provided with ink cartridges, contains the reactants mix with transparent ink. The product manufacture only needs to insert the cartridges in the printing machine, which prints the required layers (with/without barrier layer), on the package of the perishable product, after packaging, and by so activate the temperature indicator. The QR barcode (FIG. 3) will be printed separately on the package beside (or around) the indicator.

Another possible method for indicating dependence of perishable products comprises: two label system in which a separating film is place between the top and base labels, so that the two labels can be attached without being activated. The activation is manual by pulling the separating film and attaching the remain label. This manual activation option can be used in the event that food for example is packed outside factory, so that automated activation is impossible, or where the end user opens a vacuum package of food and wants to know after the opening the vacuum package for how long can he eat the food.

EXAMPLE 1

A preferred embodiment in accordance with a preferred embodiment of the present invention is using the operation mechanism of chelating agents color change. The reactant that is being chosen is a chelating agent 2,2'-Dipyridil. It is known that 2,2'-Dipyridil is a reactant for Fe ion and change color for colorless to red. The structure of the indicator is as according to option 1:

Therefore, a temperature indicator was built in accordance to the present invention while the first reactant solution (provided on the upper layer) was 2,2'-Dipyridil, and the second reactant that is provided in base layer 18 was—Iron (II) chloride (water solution, 5 mg/ml). The barrier layer was selected to be clear ink of substantially 10 microns in thickness. The starting color is colorless, and it changes to red at the end of the reaction process. The indicator was design as a TTI for 48 hours at 5° C. The temperature abuse allow was no more than 6 hours at ±3° C.

The system described herein was test at 5° C., 8° C., 2° C. The indicator was periodically removed from incubator for scanning of color change. The scanning device massages from the tests are shown in table 1.

TABLE 1

| Temperature | time (Hour) | | | | |
| --- | --- | --- | --- | --- | --- |
| ° C. | 6 | 12 | 24 | 36 | 48 |
| 5 | Good for use (color almost colorless) | Good for use (color very light pink) | Good for use (color light pink) | Good for use (color pink) | Not to use (color red) |
| 8 | Damage H-temp (color very light pink) | | | | |
| 2 | Damage L-temp (color colorless) | | | | |

Table 1 clearly shows the performance of the system as a TTI and TI indicator illustrated herein as a preferred embodiment of the present invention can preferably show the end of expiration date for perishable product, and any temperature abuse.

EXAMPLE 2

Another preferred embodiment in accordance with a preferred embodiment of the present invention is the use the operation mechanism of PH dependent color change indicators. The structure of the indicator is according to option 3.

The first active compound is 10% bromophenol blue sodium salt (BPB-Na) solution micro capsuled mixed in ink in one cartridge.

The second active compound is 20% of Citric acid mix in ink in the second cartridge. The color changes are blue-green-yellow-red as function of the temperature exposure.

The indicator was design as a TTI for 48 hours at 20° C. The temperature abuse allow was no more than 4 hours at ±5° C.

The system described herein was tested at 20° C., 25° C., 15° C. The indicator was periodically removed from incubator for scanning of color change. The scanning device massages from the tests are shown in table 2.

TABLE 2

| Temperature | time (Hour) | | | | |
|---|---|---|---|---|---|
| ° C. | 4 | 12 | 24 | 36 | 48 |
| 20 | Good for use (color blue green) | Good for use (color green) | Good for use (color yellow) | Good for use (color orange) | Not to use (color red) |
| 25 | Damage H-temp (color green) | | | | |
| 15 | Damage L-temp (color blue) | | | | |

Table 2 clearly shows the performance of the system as a TTI and TI indicator illustrated herein as a preferred embodiment of the present invention can preferably show the end of expiration date for perishable product, and any temperature abuse

EXAMPLE 3

Another preferred embodiment in accordance with a preferred embodiment of the present invention is the use the operation mechanism of free radical generators destring dye color reaction. The structure of the indicator is option 1. The reactants that were chosen were: the first compound, Leuco Malachite Green, and the second compound was 2-Nitrobenzaldehide. A 0.3 ml of solution of the leuco Malachite Green in THF (c.60 mg/ml) was made, mixed with glue and coated on the bottom of top label. A 0.3 ml solution of the 2-Nitrobenzaldehide in THF (c.30 mg/ml) was made, mix with ink and printed on the base label. A barrier layer of 5-micron clear ink was printed on the second compound layer.

The indicator was designed as a TTI for 48 hours at −5° C. The temperature abuse allowed was no more than 12 hours at ±2° C.

The system described herein was test at −5° C., −2° C., −7° C. The indicator was periodically removed from incubator for scanning of color change. The scanning device massages from the tests are shown in table 3.

TABLE 3

| Temperature | time (Hour) | | | |
|---|---|---|---|---|
| ° C. | 12 | 24 | 36 | 48 |
| −5 | Good for use (color green) | Good for use (color light green) | Good for use (color very light green) | Not to use (colorless) |
| −2 | Damage H-temp (color light green) | | | |
| −7 | Damage L-temp (color strong green) | | | |

Table 3 clearly shows the performance of the system as a TTI and TI indicator illustrated herein as a preferred embodiment of the present invention can preferably show the end of expiration date for perishable product, and any temperature abuse.

EXAMPLE 4

Another preferred embodiment in accordance with a preferred embodiment of the present invention is using the operation mechanism of reduction agent color change reaction. The structure of the indicator is as option 2. The reactants that were chosen, the first compound sodium sulfite, and the second one malachite green. The 5% solution of sodium sulfite in THF (c.60 mg/ml) and was mixed with glue and coated on the bottom of top label.

The 1% solution malachite green in THF (c.30 mg/ml) and was mixed with ink and printed on the perishable product package. The barrier layer (also printed on the perishable product package) was 5 microns thick.

The indicator was designed as a TTI for 200 hours at 40° C. The temperature abuse allowed was no more than 20 hours at ±5° C.

The system described herein was test at 40° C., 45° C., 35° C. The indicator was periodically removed from incubator for scanning of color change. The scanning device massages from the tests are shown in table 4.

TABLE 4

| Temperature | time(Hour) | | | | |
|---|---|---|---|---|---|
| ° C. | 20 | 50 | 100 | 150 | 200 |
| 40 | Good for use (color green) | Good for use (color light green) | Good for use (color very light green) | Good for use (color very light green) | Not to use (colorless) |
| 45 | Damage H-temp (color light green) | | | | |
| 35 | Damage L-temp (color strong green) | | | | |

Table 4 clearly shows the performance of the system as a TTI and TI indicator illustrated herein as a preferred embodiment of the present invention can preferably show the end of expiration date for perishable product, and any temperature abuse.

EXAMPLE 5

Another preferred embodiment in accordance with a preferred embodiment of the present invention is the use the operation mechanism of metal foil acid etching color change reaction. The structure of the indicator is as option 1. The reactants that were chosen were: the first compound, Hydrochloric acid, and the second compound Tin. A 1% of solution of was mix with glue and coated on the bottom of top label. A red dye layer of ink was printed on the base label. A Tin foil 20 microns was coated over the red ink layer.

The indicator was design as a TTI for 20 hours at 50° C. The temperature abuse allow was no more than 6 hours at ±10 C.

The system described herein was tested at 50° C., 60° C., 40° C. The indicator was periodically removed from incubator for scanning of color change. The scanning device massages from the tests are shown in table 5.

TABLE 5

| Temperature | time (Hour) | | | |
|---|---|---|---|---|
| ° C. | 6 | 10 | 15 | 20 |
| 50 | Good for use (color very light pink) | Good for use (color light pink) | Good for use (color pink) | Not to use (color red) |
| 60 | Damage H-temp (color light pink) | | | |
| 40 | Damage L-temp (color white) | | | |

Table 5 clearly shows the performance of the system as a TTI and TI indicator illustrated herein as a preferred embodiment of the present invention can preferably show the end of expiration date for perishable product, and any temperature abuse.

A preferred temperature range for integrated TTIs responding to both time and temperature, or for TTIs, that respond primarily to temperature, will depend on their intended use. The TTI for regular products range is from −30° C. C, and above.

In order to obtain the widest possible range of indicator response in the indicating device, the device can contain a mixture of different indicator compounds, each of which undergoes a series of color changes during thermal history development. Alternatively, the device can consist of adjacent strips containing different acetylenic compositions with different activities.

Without further elaboration, it is believed that one skilled in the art, using the preceding description, can utilize the present invention to its fullest extent. The preceding preferred specific embodiments are, therefore, to be construed as merely illustrative, and not limitative of the remainder of the disclosure in any way whatsoever.

The entire disclosure of all patent applications, patents, and publications cited herein are hereby incorporated by reference.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A system for accurate measurement of the true condition of a temperature sensitive product; said system comprising a scanning device, a QR barcode, and an indicator capable of exhibiting an irreversible color change, which is time-temperature dependent; said indicator comprising an upper layer and a base layer, which are initially provided separately and adapted to be attached to each other in order to provide a triggering mechanism allowing a chemical reaction to start at a predetermined instant; said QR barcode being printed separately on a package of the temperature sensitive product beside or around the indicator; said system using a software installed in said scanning device; said software being programmed to identify a specific type of the temperature sensitive product and other related data by the QR barcode; said software being programmed to compare scanned color values of the indicator at any time to a data base of color values for the temperature sensitive product and to generate an alert or digital report according to predetermined matching color values of the indicator and the temperature sensitive product, wherein the matching color values are indicative of temperature and duration abuse for the temperature sensitive product, in case temperature abuse has occurred, and/or when the shelf life has ended, such that the indicator performs both as a time-temperature-indicator and a virtual temperature-indicator at the same time.

2. The system as claimed in claim 1, wherein said upper layer is coated on a bottom side with a glue mixed with a first reactant of said chemical reaction, and a top side of said base layer is printed with a layer of clear barrier, below which is printed a layer of ink mixed with a second reactant of said chemical reaction, and a bottom side of said base layer is coated with a layer of self-adhesive glue to allow attachment to the package.

3. The system as claimed in claim 2, wherein said time-temperature indicator changes its color irreversibly due to the chemical reaction between the first reactant and second reactant; said first reactant and second reactant being chosen from a group consisting of: redox reactions, chelating agents, PH sensitive dye, and free radical generators that usually form radical that destroys the dye molecule.

4. The system as claimed in claim 1, wherein said scanning device is adapted to generate an electronic alert signal and transmit/communicate the electronic alert signal to other electronic devices via a wired or wireless connection.

5. The system as claimed in claim 1, wherein said software is programmed to communicate with, and receive communication from other electronic devices.

\* \* \* \* \*